(12) United States Patent
Steger et al.

(10) Patent No.: US 7,052,499 B2
(45) Date of Patent: May 30, 2006

(54) METHOD AND APPARATUS FOR BONE FRACTURE FIXATION

(75) Inventors: Shon D. Steger, Jacksonville, FL (US); Stephen M. Herrington, Orange Park, FL (US); Brian S. Schumacher, Jacksonville, FL (US); Kevin T. Stone, Jacksonville, FL (US); Jeffrey A. Duncan, Jacksonville, FL (US)

(73) Assignee: Walter Lorenz Surgical, Inc., Jacksonville, FL (US)

( * ) Notice: Subject to any disclaimer, the term of this patent is extended or adjusted under 35 U.S.C. 154(b) by 636 days.

(21) Appl. No.: 10/081,166

(22) Filed: Feb. 22, 2002

(65) Prior Publication Data

US 2002/0128654 A1    Sep. 12, 2002

Related U.S. Application Data

(63) Continuation-in-part of application No. 10/047,520, filed on Oct. 29, 2001, now abandoned.

(51) Int. Cl.
*A61B 17/80* (2006.01)

(52) U.S. Cl. .................................................. 606/69

(58) Field of Classification Search ................ 606/60, 606/61, 69, 70, 71, 213, 215
See application file for complete search history.

(56) References Cited

U.S. PATENT DOCUMENTS

| 1,105,105 | A | 7/1914 | Sherman |
| 2,489,870 | A | 11/1949 | Dzus |
| 2,494,229 | A | 1/1950 | Collison |
| 2,631,584 | A | 3/1953 | Purificato |
| 3,488,779 | A | 1/1970 | Christensen |
| 4,219,015 | A | 8/1980 | Steinemann |
| 4,429,690 | A | 2/1984 | Angelino-Pievani |
| 4,484,570 | A | 11/1984 | Sutter et al. |
| 4,708,132 | A | 11/1987 | Silvestrini |
| 4,903,691 | A | 2/1990 | Heinl |
| 4,959,065 | A | 9/1990 | Arnett et al. |
| 4,973,332 | A | 11/1990 | Kummer |
| 5,108,395 | A | 4/1992 | Laurain |

(Continued)

FOREIGN PATENT DOCUMENTS

DE    867 422    7/1949

OTHER PUBLICATIONS

A Biomechanical Study of Median Sternotomy Closure Techniques, European Journal of Cardio-thoracic Surgery 15, A.R. Casha, L. Yang, P.H. Kay, M. Saleh, and G.J. Cooper (1999), pp. 365-369.

(Continued)

*Primary Examiner*—David O. Reip
(74) *Attorney, Agent, or Firm*—Harness, Dickey & Pierce, P.L.C.

(57) ABSTRACT

An elongated plate for coupling severed bone regions comprising at least one bridge region, the at least one bridge region terminating in at least two bone fixation regions. The at least two bone fixation regions each contain at least one aperture for receiving a suitable fastening device for securing the elongated plate to the bone regions to be coupled. The bridge region may be configured so as to be easily severed by a suitable severing device such as surgical scissors. The elongated plate and fastening device may be formed from a bio-compatible or bio-resorbable material.

48 Claims, 10 Drawing Sheets

U.S. PATENT DOCUMENTS

| | | | |
|---|---|---|---|
| 5,108,399 A | | 4/1992 | Eitenmuller et al. |
| 5,129,899 A | | 7/1992 | Small et al. |
| 5,147,363 A | | 9/1992 | Harle |
| 5,151,103 A | | 9/1992 | Tepic et al. |
| 5,180,382 A | | 1/1993 | Frigg et al. |
| 5,269,784 A | | 12/1993 | Mast |
| 5,303,718 A | | 4/1994 | Krajicek |
| 5,336,224 A | * | 8/1994 | Selman .................. 606/69 |
| 5,358,367 A | | 10/1994 | Yang |
| 5,372,598 A | | 12/1994 | Luhr et al. |
| 5,403,136 A | | 4/1995 | Mathys |
| 5,413,577 A | | 5/1995 | Pollock |
| 5,474,551 A | | 12/1995 | Finn et al. |
| 5,505,731 A | | 4/1996 | Tornier |
| 5,520,690 A | | 5/1996 | Errico et al. |
| 5,569,247 A | | 10/1996 | Morrison |
| 5,591,167 A | | 1/1997 | Laurain et al. |
| 5,601,553 A | | 2/1997 | Trebing et al. |
| 5,601,554 A | | 2/1997 | Howland et al. |
| 5,607,427 A | * | 3/1997 | Tschakaloff .............. 606/69 |
| 5,607,428 A | | 3/1997 | Lin |
| 5,653,710 A | | 8/1997 | Harle |
| 5,676,667 A | | 10/1997 | Hausman |
| 5,709,686 A | * | 1/1998 | Talos et al. ............... 606/69 |
| 5,722,976 A | | 3/1998 | Brown |
| 6,007,538 A | | 12/1999 | Levin |
| 6,488,685 B1 | * | 12/2002 | Manderson ............... 606/69 |

OTHER PUBLICATIONS

Biomechanical Study of Sternal Closure Techniques, Wen Cheng, MD, Duke E. Cameron, MD, Karen E. Warden, PhD, James D. Fonger, MD, and vincent L. Gott, MD, Div. of Cardiac Surgery, The Johns Hopkins Medical Institutions, Baltimore, MD (1993), pp. 737-740.

Biomechanical Study of Sternal Closure Using Rigid Fixation Techniques in Human Cadavers, Wayne Ozaki, MD, Steven R. Buchman, MD, Mark D. Iannettoni, MD, and elizabeth P. Frankenburg, BS, Sections of Plastic and Reconstructive Surgery, and Cardiothoracic Surgery, University of Michigan Medical Center, Ann Arbor, MI (1998), pp. 1660-1665.

Bite Forces Before and After Surgical Correction of Mandibular Prognathism, Edward Ellis III, DDS, Gaylord S. Throckmorton, PhD, and Douglas P. Sinn, DDS, American Assoc. of Oral and Maxillofacial Surgeons (1996), pp. 176-181.

Catastrophic Hemorrhage on Sternal Reentry: Still a Dreaded Complication?, Fabrizio M. Follis, MD, Stuart B. Pett, Jr, JD, Kevin B. Miller, MD, Rose S. Wong, MD, R. Thomas Temes, MD, and Jorge A. Wernly, MD, Ann Thorac Surg 1999;68:2215-2219, 1999 The Society of Thoracic Surgeons (reprint).

Chest Wall Stabilizatin Using Plate Fixation, John E. Sherman, MD, Andrew Salzberg, MD, Noel M. Raskin, MD, and Edward J. Beattie, MD, Annals of Thoracic Surgery (Oct. 1988), pp. 467-469.

Comparison of Habitual Masticatory Cycles and Muscle Activity Before and After Orthognathic Surgery, Riad E. Youssef, DDS, Gaylord S. Throckmorton, PhD, Edward Ellis III, DDS, MS, and Douglas P. Sinn, DDS, American Assoc. of Oral and Maxillofacial Surgeons (1997), pp. 699-708.

The Healing Sternum: A Comparison of Osseous Healing With Wire Versus Rigid Fixation, Larry A. Sargent, MD, Alan E. Seyfer, MD, Jeffery Hollinger, DDS, PhD, Roger M. Hinson, and Geoffrey M. Graeber, MD, Plastic Surgery Service, Walter Reed Army Medical Center and Institute of Research, and US Army Institute of Dental Research, Washington, D.C. (Apr. 5, 1991), pp. 490-494.

Improved Sternal Fixation in the Correction of Pediatric Pectus Excavatum, Michael L. Bentz, MD, Marc I. Rowe, MD, and Eugene S. Wiener, MD, Case Report (1994) by Little, Brown and Company, pp. 638-641.

Improvement of Maximum Occlusal Forces After Orthognathic Surgery, Gaylord S. Throckmorton, PhD, Peter H. Buschang, PhD, and Edward Ellis III, DDS, 1996 American Assoc. of Oral and Maxillofacial Surgeons, 54:1080-1086.

Internal Fixation of the Sternum in Median Sternotomy Dehiscence, Christopher W. Chase, MD, John D. Franklin, MD, Daryl P. Guest, MD, and Donald E. Barker, MD, Dept. of Surgery at Univ. of Tenn. College of Medicine (Nov. 25, 1998), pp. 1667-1673.

Mechanical analysis of Midline Sternotomy Wound Closure, Walter E. McGregor, MD, Dennis R. Trumble, MS, and James A. Magovern, MD, The Journal of Thoracic and Cardiovascular Surgery, vol. 117, No. 6, pp. 1144-1150.

Median Sternotomy Dehiscence, William S. Stoney, MD, et al., The Annals of Thoracic Surgery, vol. 26, No. 5, Nov. 1978, pp. 421-426.

Median Sternotomy Wound Dehiscence: A Retrospective Case Control Study of Risk Factors and Outcome, A. J. Bryan, et al., Dept. of Cardiac Surgery, University Hospital of Wales, Cardiff, UK (1992), pp. 305-308.

Non-Union of Fractures of the Sternum, I. I. Mayba, MD, Winnipeg, Manitora, Canada, The Journal of Bone and Joint Surgery, Incorporated (1985), pp. 1091-1093.

Open Fixation of Sternal Fracture, Jerry Kitchens, MD, and J. David Richardson, MD, FACS, Louisville, Kentucky; Surgery, Gynecology & Obstetrics, Oct. 1993, Vo. 177, pp. 176-177.

Paramedian Sternal Bone Plate Reinforcement and Wiring for Difficult Sternotomy Wounds, E. Clyde Smoot, MD, and Darryl Weiman, MD (1998) by Lippincott Williams & Wilkins, pp. 464-467.

A Polyurethane Foam Model for Characterizing Suture Pull-Through Properties in Bone; Joseph E. Hale, Donald D. Anderson, and Greg A. Johnson, Biomechanics Laboratory, Minneapolis Sports Medicine Center, Minneapolis, MN, www.asb-biomech.org/abstracts99/133 (4 pgs) (reprint).

Repair of Sternal Dehiscence Using a Harrington Compression System, Mark D. Miller, P.A.-C, Robert G. Johnson, MD, and Jerome Naifeh, MD, Ann Thorac Surg 45:684-685, Jun. 1988.

Rigid Internal Fixation of the Sternum in Postoperative Mediastinitis, Lawrence J. Gottlieb, MD, et al., Arch Surg/vol. 129, May 1994, pp. 489-493.

Sternal Plating for the Treatment of Sternal Nonunion, Steven C. Hendrickson, MD, et al., Divisions of Cardiothoracic Surgery, Plastic and Maxillofacial Surgery, and Orthopaedic Surgery, Dept. of Surgery, Duke Univ. Medical Center and Durham Veterans Administration Hospital, Durham, NC (1996), pp. 512-518.

Sternal Slavage With Quantitative Bacteriology and Rigid Plate Fixation in Postoperative Mediastinitis: A 10 Year Experience, David H. Song, MD, et al., American Assoc. of Plastic Surgeons—79th Annual Meeting (May 7-10, 2000), 3 Pages.

Prophylactic Rigid Plate Fixation for High Risk Sternotomies, David H. Song, MD, The University of Chicago Plastic and Reconstructive Surgery (Feb. 23, 2001) 16 Pages.

Superior Sternal Cleft: Construction With A Titanium Plate, Anita Hazaari, F.R.C.S., et al., Frenchay Hospital and Bristol Children's Hospital, Bristol, UK (Feb. 3, 1997), pp. 167-170.

Update on Sternal Osteosynthesis, Josef G. Vincent, MD, How To Do It, Institute of Thoracic, Cardiac and Vascular Surgery, Saint Radboud Univ. Hospital, Nijmegen, The Netherlands (Mar. 14, 1985), pp. 216-218.

* cited by examiner

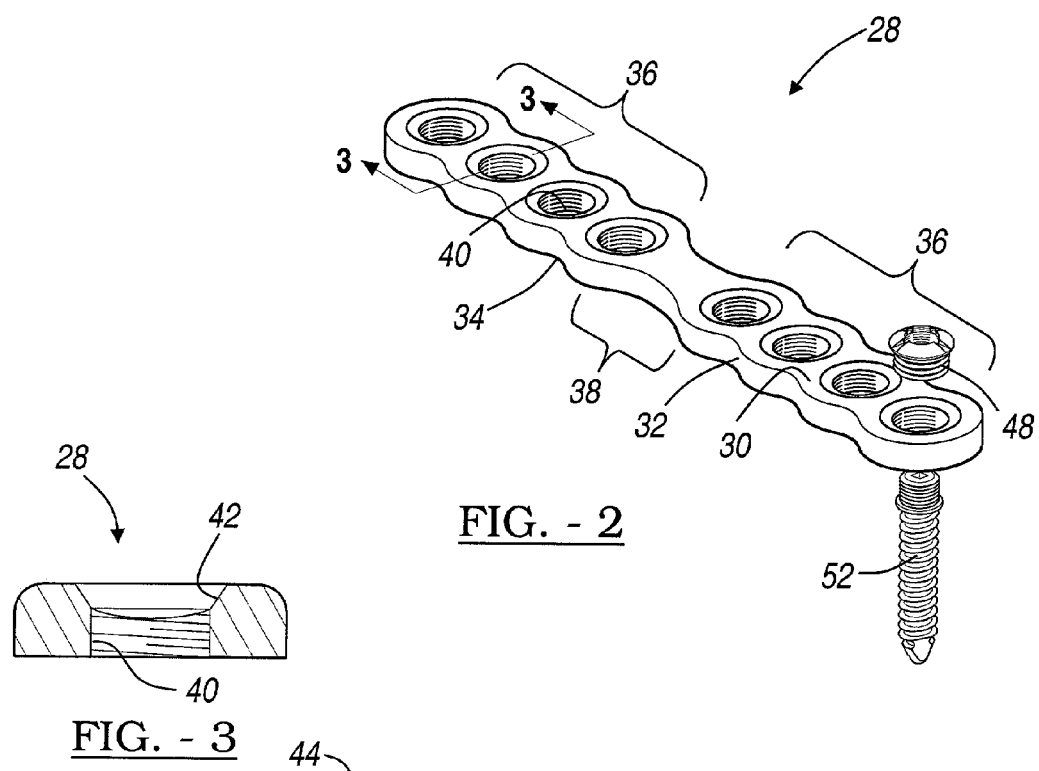
FIG. - 2
FIG. - 3
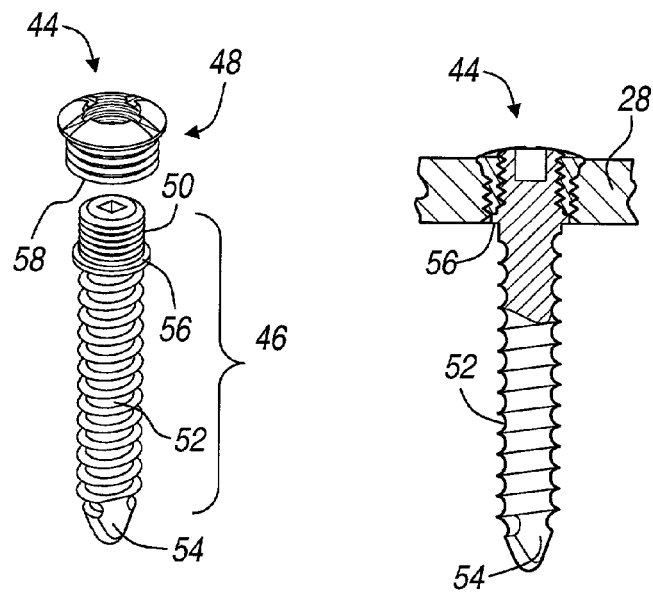
FIG. - 4
FIG. - 4a

METHOD AND APPARATUS FOR BONE FRACTURE FIXATION

CROSS-REFERENCE TO RELATED APPLICATIONS

This application is a continuation-in-part of U.S. patent application Ser. No. 10/047,520 filed on Oct. 29, 2001, now abandoned, which is a continuation of U.S. patent application Ser. No. 09/394,287 filed on Sep. 10, 1999 (now U.S. Pat. No. 6,325,803), which is a continuation-in-part of U.S. patent application Ser. No. 09/025,140 filed on Feb. 18, 1998 (now U.S. Pat. No. 6,129,728).

FIELD OF THE INVENTION

The present invention relates to surgical applications for the repair of bone fractures and deformities. More particularly, the present invention relates to a method and apparatus for securing two severed bone portions in a relatively fixed relationship to each other.

BACKGROUND OF THE INVENTION

In various orthopedic surgical procedures, it is necessary to align and secure two severed bone portions in a relatively fixed relationship to each other. For example, it is often necessary to establish such a secured relationship after a bone has been fractured as a result of either natural causes or physician intervention. To ensure that the bone can regenerate in the proper orientation and fuse the fracture, it is important that the bone portions be fixed in the desired position during bone regeneration.

It is known in the art to provide metal plates for the repair of bone fractures. The plates are generally secured to the fractured bone portions with fasteners such as screws. Among other applications, the plates and fasteners are used to provide rigid stabilization of sternum fractures. The plates conventionally employed for sternum osteosynthesis generally comprise small, generally flat, elongated sections of metal. The sections contain round and perhaps elongated screw holes at various points along their lengths for fastening the sections to bone.

In one technique for sternum reconstruction, a plate having one or more apertures is drawn against the surface of the sternum so that the plate spans the severed region of the sternum. The plate is then bent into shape and secured to the sternum using a plurality of fasteners seated within the apertures. Subsequently, the fasteners and plate may be removed to allow surgical access to the sternum (e.g., to treat vital organs within the thoracic cavity). Finally, the same plate or a new plate is again fastened to the sternum through engagement of the fasteners with the sternum.

While known systems utilizing plates and fasteners for aiding the osteosynthesis of severed bone regions have proven to be acceptable for certain applications, such systems are nevertheless susceptible to improvements that may enhance their performance. In this regard, many known systems require time consuming attachment. Additionally, known systems which necessitate the insertion, removal, and subsequent reinsertion of fasteners into the bone negatively affect fastener purchase. Furthermore, many known systems do not facilitate cutting of the plate to provide expedited physician access to the area or cavity previously enclosed by the plate.

SUMMARY OF THE INVENTION

The present invention relates to an apparatus and method for reapproximating and securing portions of severed bone. Reapproximation of the severed bone portions is carried out using a bone reapproximation device. The reapproximation device is able to laterally hook and reapproximate the separated bone regions. Once reapproximated, the bone regions are coupled using an elongated plate. The elongated plate is comprised of at least two bone fixation regions with a bridge region disposed between the bone fixation regions. Each bone fixation region contains at least one receptor used to receive a fastener suitable for securing the elongated plate to the bone portions to be coupled. Both the elongated plate and the fastening devices may be either bio-resorbable or bio-compatible.

The fasteners preferably have a main body portion with an upper shaft portion and a lower shaft portion. The fasteners further include a head member removably attached to the upper shaft portion. Once secured to the bone surface due to interaction with the fasteners, the elongated plate may be removed from engagement with the bone surface by removing the head member and subsequently raising the plate from the bone surface. The fastener configuration allows for removal of the elongated plate without the need for removing the main body from the bone, thus allowing the main body and hole within the bone to be used again in the future to secure an elongated plate to the bone surface.

The elongated plate of the present invention may be severed so as to permit the rapid separation of the bone portions previously secured by the elongated plate. The elongated plate may be severed using any suitable cutting device, such as surgical scissors. Severing of the plate using surgical scissors is facilitated due to the presence of a bridge portion that is specifically configured to allow for such engagement. For example, the bridge portion may be raised or tapered so as to create a gap between the bone surface and the bridge portion, the gap permitting engagement of the bridge region by surgical scissors. The bridge portion may also be weakened or contain a notch to further aid in severing the bridge portion.

The elongated plate of the present invention may also have numerous bridge portions and bone fixation regions arranged in a variety of shapes so as to produce an elongated plate with a configuration capable of coupling a large region of severed bones, the bones terminating at various different angles to each other. To aid in the coupling of such severed bone regions, the bridge regions and the bone fixation regions may extend at a variety of different angles. Further, the bone fixation regions and the bridge regions may be in differing planes so as to couple severed bone regions that terminate at differing planes to each other.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

FIG. 1 illustrates a previously severed sternum coupled by an elongated plate in one possible placement scheme according to the teachings of a first preferred embodiment of the present invention.

FIG. 2 is a perspective view of the elongated plate of FIG. 1.

FIG. 3 is a cross-sectional view taken along line 3—3 of FIG. 2.

FIG. 4 is an exploded perspective view of a fastener used to secure the elongated plate of FIG. 1 to a severed bone portion.

FIG. 4a is a side view of the fastener of FIG. 4, the fastener seated within an aperture of the elongated plate of FIG. 1.

DETAILED DESCRIPTION OF THE PREFERRED EMBODIMENTS

The following description of the preferred embodiments is merely exemplary in nature and is in no way intended to limit the invention, its application, or uses.

Figure 1:
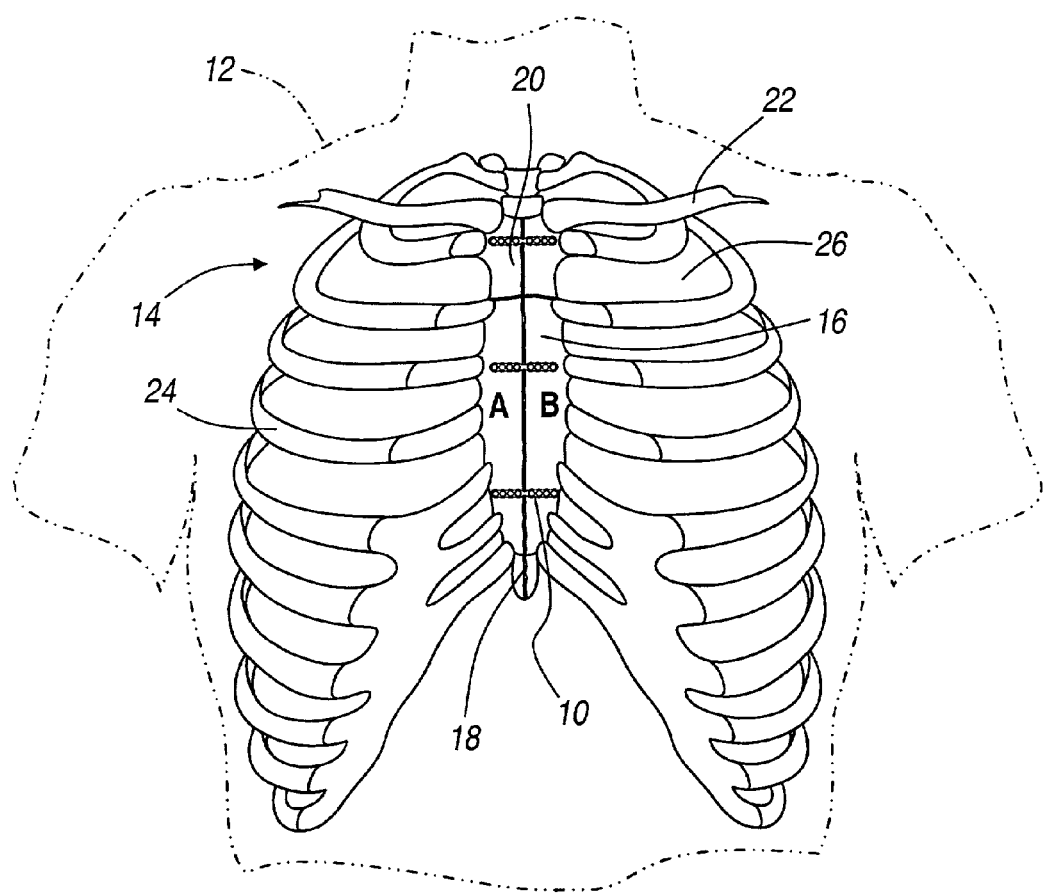
FIG. 1 is a perspective postoperative anterior illustration of a human thorax. Specifically.

Referring to FIG. 1, a system constructed in accordance with a preferred embodiment of the present invention is generally identified with reference numeral 10. The system 10 is shown operatively associated within a human body 12 and specifically a human thorax 14. However, it will become apparent to those skilled in the art that certain aspects of the present invention have applicability to other surgical applications.

The anterior of the thorax 14 is formed by a sternum 16, xyphoid 18, and manubrium 20, while the posterior and lateral surfaces are formed by a clavicle 22 and a rib cage 24. The sternum 16, as shown, has previously undergone a medical procedure known as a median sternotomy. As a result of this procedure, the sternum 16 has been severed, thus permitting physician access to the tissues or organs located in thoracic cavity 26. However, the sternum 16 has since been reapproximated with previously severed portions A and B now bound together by the system 10 of the present invention.

With continued reference to FIG. 1 and additional reference to FIGS. 2 through 22, the system 10 of the present invention is shown to include an elongated plate 28. The elongated plate 28 is shown to include an upper surface 30, a lower surface 32, and a perimeter surface 34. The perimeter surface 34 may be specifically defined, as seen in FIG. 2, or may simply be the point at which the upper surface 30 and the lower surface 32 meet. The elongated plate 28 is divided into varying regions such as at least two bone fixation regions 36 and at least one bridge region 38.

The bridge region 38 joins the bone fixation regions 36. Each bone fixation region 36 defines at least one aperture 40. The apertures 40 may be threaded or simply formed as non-threaded through holes. The apertures 40 may extend symmetrically from the bridge region 38 or may be arranged asymmetrically. Further, the apertures 40 may optionally include an oval countersink 42. The apertures 40 may be internally threaded. The apertures 40 are adapted to receive a fastener 44 for interconnecting the elongated plate 28 with a severed bone region, such as severed halves A and B of the sternum 16. More specifically, the bridge region 38 spans the fracture while bone fixation regions 36 are fastened to the bone regions on either side of the fracture once the severed halves A and B have been reapproximated.

The elongated plate 28 described in any of the embodiments of the present invention may be made of a variety of bio-resorbable materials. One resorbable material of particular interest is marketed by Biomet, Inc. (Warsaw, Ind.) under the tradename LACTOSORB®. LACTOSORB® is an absorbable co-polymer synthesized from all-natural ingredients: 82% L-lactic acid and 18% glycolic acid, and is substantially amorphous (i.e., without crystallinity), meaning that its degradation is uniform, precluding the crystalline release associated with degrading copolymers that have been associated with late inflammatory reactions. Furthermore, the LACTOSORB® copolymer ratio permits the polymer to retain most of its strength for six to eight weeks. Such a time period is appropriate for healing, but not so long as to raise concerns about long-term stress shielding of bone. In addition to LACTOSORB®, other resorbable materials may be used such as PLA, PGA, and others including various polymers, ceramics, etc.

In addition to being made from bio-resorbable materials, the elongated plate 28 may also be made from a variety of bio-compatible materials. Examples of bio-compatible materials that may be used are the implantable plastics PEEK or PET. In addition to PEEK or PET, implantable surgical metals may also be used. Alloys that may be implanted are, but not limited to, stainless steel, titanium, or cobalt chrome molybdenum. Specifically, commercially pure, grade 2 or 4 titanium may be used. The elongated plate 28 may be inelastically deformable so as to retain its shape once contoured to cooperate with the shape of the bone regions to be secured.

With additional reference to FIG. 4, the fastener 44 of the present invention is shown to generally include a main body 46 and a head member 48. The main body 46 includes an upper shaft portion 50 and a lower shaft portion 52. The lower shaft portion 52 is externally threaded, fluted, and preferably fitted with a pointed end portion 54 so as to permit self-drilling and/or self-tapping engagement of the sternum 16 by fastener 44. Insertion of the lower shaft portion 52 into sternum 16 is limited by a flange 56 interdisposed between the upper and lower shaft portions 50 and 52. The upper shaft portion 50 is also externally threaded and adapted to engage an internally threaded aperture 58 of the head member 48. The head member 48 is externally threaded for engaging one of the plurality of internally threaded apertures 40 of the elongated plate 28.

Fastener 44 may be formed of a suitably rigid biocompatible material. However, if the intent is to insert fastener 44 into the bone for a temporary period of time, it may be formed from a bio-resorbable material. Fasteners 44 formed from bio-resorbable materials degrade within the body, thus eliminating the need for subsequent removal of the fasteners 44.

In one application, the thread pitches of the upper shaft portion 50, lower shaft portion 52, and the thread pitch of the external threads of the head member 48 are common. The external threads of the head member 48 and the externally threaded lower shaft portion 52 have a common thread lead. In the exemplary embodiment illustrated, the externally threaded lower shaft portion 52 has a single lead configuration while the external threads of the upper shaft portion 50 and head member 48 have a double lead configuration.

Figure 5:
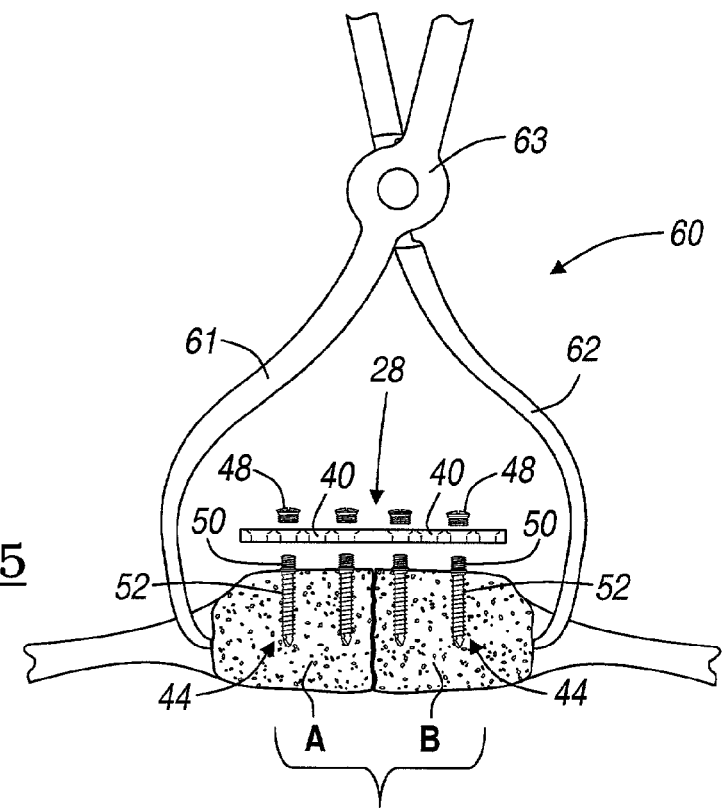
FIG. 5 is a partially sectioned side view of the elongated plate of FIG. 1 illustrating the cooperation of the elongated plate with the fasteners of FIG. 4 for securing the elongated plate to the previously severed sternum halves, the previously severed sternum halves have been reapproximated using the illustrated surgical forceps.

In use, before the elongated plate 28 may be secured to severed halves A and B of sternum 16, the severed halves A and B must be reapproximated. Reapproximation of severed sternum halves A and B may be carried out using, as seen in FIG. 5, a reapproximation device, preferably in the form of surgical forceps 60. The surgical forceps 60 are comprised of two jaws 61, 62 that are interconnected at actuation point 63. The jaws 61, 62 are able to laterally hook separated bone halves A and B. By pivoting the jaws 61, 62 about actuation point 63, a physician is able to decrease the distance between the jaws 61, 62 and thus, in turn, decrease the distance between the separated bone halves A and B.

Once the separated bone halves A and B have been reapproximated, a malleable template (not shown) may be positioned on the bone surfaces of severed halves A and B, and bent to the general shape of the cooperating bone surface. Next, the elongated plate 28 is bent to approximately the shape of the template and positioned on the bone surfaces to be coupled so that certain apertures 40 may be selectively used as a guide for drilling holes (not specifically shown) in the bone surfaces for receiving the fasteners 44.

A first of the fasteners 44 is passed through a selected one of the apertures 40 and rotated so that the externally threaded lower portion 52 is driven into the hole (not shown) in one of the halves A or B of the sternum 16. For example, as the externally threaded lower portion 52 of the fastener 44 is driven into the sternum 16, the external threads of the head member 48 simultaneously engage the internally threaded aperture 40 of the elongated plate 28. This is possible as a result of the common thread lead shared between the lower portion 52 and the head member 48.

Additional fasteners 44 are used to interconnect the elongated plate 28 with the sternum 16 in a substantially identical manner. As shown in FIG. 5, four fasteners are used to interconnect the elongated plate 28 with the sternum 16. However, it will become appreciated by those skilled in the art that any number of fasteners 44 may be employed depending on a particular application. In one application, the order of the fastener insertion linearly progresses along the elongated plate 28 from one end to the second end. As additional fasteners are inserted through apertures 44 so as to engage the sternum 16, the elongated plate 28 is drawn into its operative position adjacent to the sternum 16.

After the elongated plate 28 has been secured into place, it may be necessary to remove the plate 28 so as to allow a physician to re-separate the sternum 16 and gain access to either the sternum 16 or the thoracic cavity 26 to provide treatment (e.g., removal of a cancerous growth). To facilitate removal of the elongated plate 28, the head members 48 of each of the threaded fasteners 44 are unthreaded from their respective upper portions 50. When the elongated plate 28 is removed, it retains its shape due to the inelastic deformation. As seen in FIG. 5, the use of elongated faster 44 is advantageous because it allows the elongated plate 28 to be removed while the lower portion 52 remains in place. This retains the integrity of each hole formed in the bone and eliminates the need to remove and re-insert different fastening devices into the bone each time the elongated plate is removed and re-seated.

When the surgical procedure is complete, the separated halves A and B of the sternum 16 are again reapproximated using the surgical forceps 60 in the manner described above. Once the separated halves A and B of sternum 16 are reapproximated to a desired distance, the halves A and B are held into place by replacing elongated plate 28. The elongated plate 28 is replaced by inserting the upper portions 50 of the fasteners 44 through the selective apertures 40 and simultaneously threading the internal threads of the aperture 40 with the external threads of the upper portion 50 and the external threads of the head member 48 with the internal threads of the aperture 40. Because fasteners 44 are not removed from the bone after initial insertion, fastener/bone purchase is not compromised.

Figure 6:
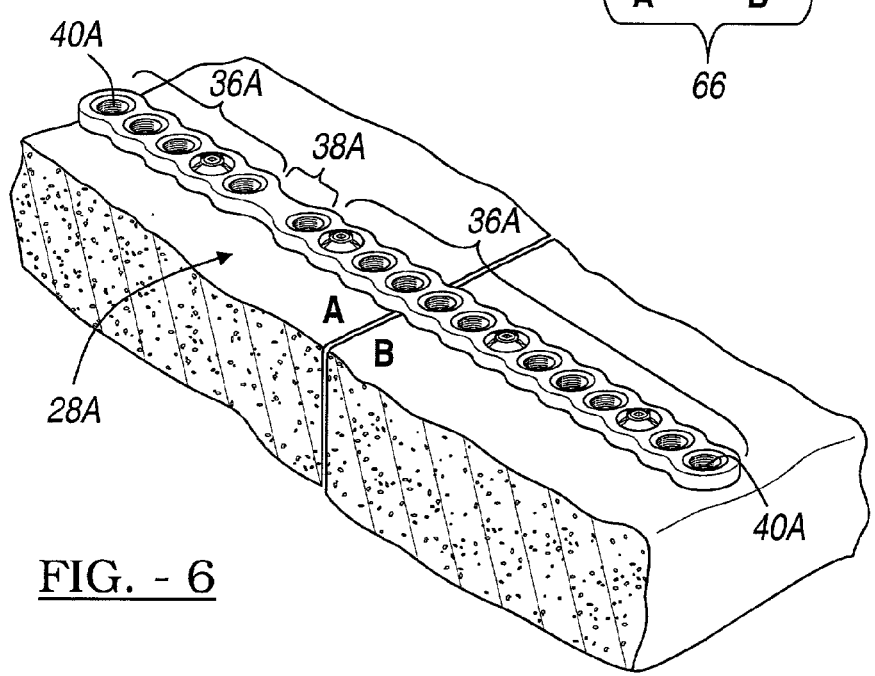
FIG. 6 is a perspective view of an elongated plate according to an additional embodiment of the present, the elongated plate having an extended number of apertures with the bridge region spanning a solid bone region.

Referring to FIG. 6, an elongated plate 28A according to the teachings of a second preferred embodiment of the present invention is shown. Elongated plate 28A is generally similar to elongated plate 28 and thus a detailed description of elongated plate 28A is not necessary. However, unlike elongated plate 28, elongated plate 28A contains an extended bone fixation region 36A having a plurality of apertures 40A and a bridge region 38A that does not span the actual bone fracture region. It must be noted that any of the other embodiments of the current invention may be configured to have an extended bone fixation region 36A and a bridge region 38A that does not span the actual bone fracture region.

Figure 7:
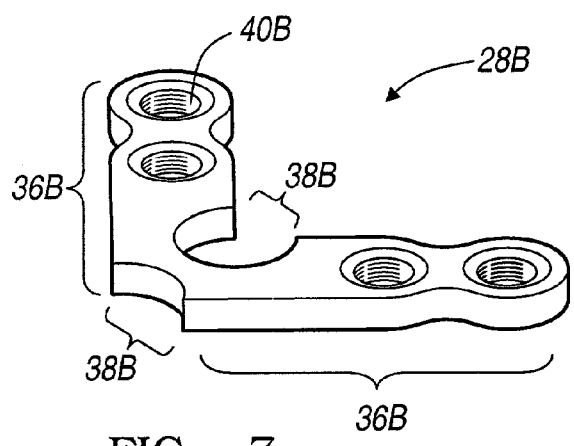
FIG. 7 is a perspective view of an elongated plate according to another embodiment of the present invention, the bridge region of the elongated plate being angled.

Elongated plate 28B is illustrated in FIG. 7 and is another embodiment of the present invention. Elongated plate 28B is generally similar to elongated plate 28 and thus a detailed description of elongated plate 28B is not necessary. However, unlike elongated plate 28, the bridge region 38B of elongated plate 28B is angled as opposed to being linear with the bridge region 38B being longitudinally disposed at an angle relative at least one of the bone fixation regions 36B. Consequently, elongated plate 28B is well suited to coupling severed bone halves that terminate at an angle to each other. It must be noted that any of the other embodiments of the current invention may incorporate the angled bridge region 38B of plate 28B.

Figure 8:
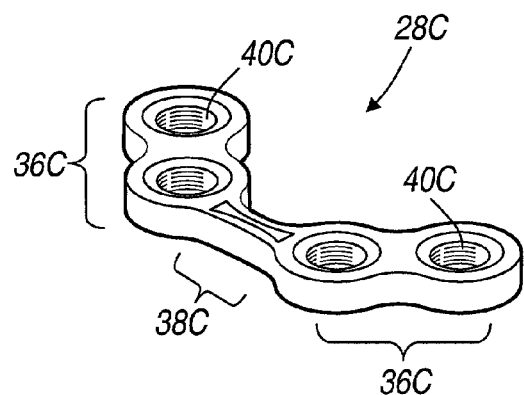
FIG. 8 is a perspective view of an elongated plate according to yet another embodiment of the present invention, the bone fixation regions extending from the bridge region at an angle.

Referring to FIG. 8, an elongated plate 28C according to the teachings of yet another embodiment of the present invention is shown. Elongated plate 28C is generally similar to elongated plate 28 and thus a detailed description of elongated plate 28C is not necessary. However, unlike elongated plate 28, the bone fixation regions 36C do not extend linearly from the bridge region 38C, but rather extend from the bridge region 38C at an angle of approximately forty-five degrees. It must be noted that any of the other preferred embodiments of the present invention may have an orientation between the bone fixation regions 36 and bridge region 38 similar to that of elongated plate 28C.

Figure 9:
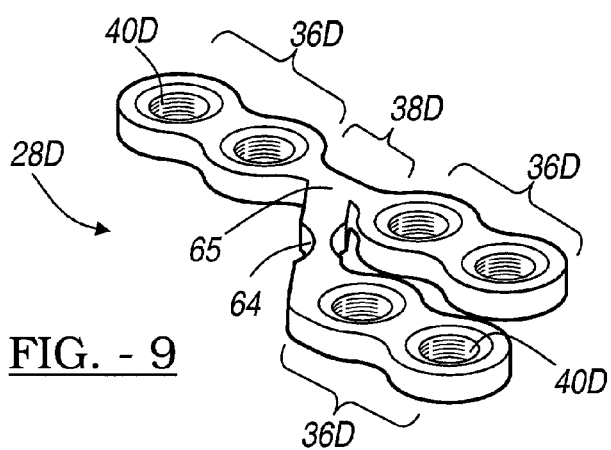
FIG. 9 is a perspective view of an elongated plate according to an additional embodiment of the present invention, the elongated plate having an adjacent bridge region extending from a mid-point of the bridge region, the adjacent bridge region terminating in a bone fixation region.

Elongated plate 28D is illustrated in FIG. 9 and is an additional embodiment of the present invention. Elongated plate 28D is generally similar to elongated plate 28 and thus a detailed description of elongated plate 28D is not necessary. Elongated plate 28D is different from plate 28 in that plate 28D includes an adjacent bridge region 64 extending from a mid-point 65 of the bridge region 38D. The adjacent bridge region 64 extends outward from mid-point 65 and is shaped so that it runs parallel with plate 28D as seen in FIG. 9. Adjacent bridge region 64 terminates in a bone fixation region 36D having one or more apertures 40D. Any of the other embodiments of the present invention may also be configured to incorporate an adjacent bridge region similar to and having the same orientation as adjacent bridge region 64.

Figure 10:
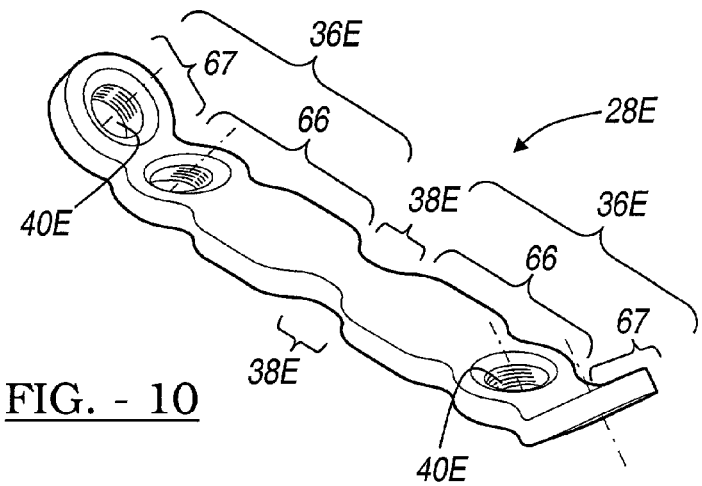
FIG. 10 is a perspective view of an elongated plate according to an additional embodiment of the present invention, the bone fixation regions having a linear portion, an angled portion, and angled apertures.

Referring to FIG. 10, an elongated plate 28E according to the teachings of an additional embodiment of the present invention is shown. Elongated plate 28E is generally similar to elongated plate 28 and thus a detailed description of elongated plate 28E is not necessary. However, unlike elongated plate 28, the bone fixation regions 36E of elongated plate 28E are divided into two portions, a portion 66 extending linearly from the bridge portion 38E and an angled portion 67 extending upwardly from the bridge region 38E. Angled portion 67 of elongated plate 28E allows plate 28E to couple bone having a non-linear surface.

Elongated plate 28E further includes angled apertures 40E for seating fasteners 44 at an angle to further aid in the closing of fractures, opening of fractures, or the sliding of one piece of bone relative to another along the fracture. The fasteners used to engage angled apertures 40E may be fasteners 44, fasteners having grooves, dimples, texturing, threads, or any other type of fastening device capable of being seated at an angle. The fasteners may be lag-type fasteners, wherein the fastener is inserted through an angled aperture and into a drilled aperture in the bone on one side of the fracture and engaging the bone on the opposite side of the fracture to draw the opposed bones together across the fracture. In this variation of the invention, the angled portion 67 extends toward (crowns over) the bone surface. It must be noted that any of the embodiments of the present invention may be configured to have angled apertures 40E or angled portion 67.

Figure 11:
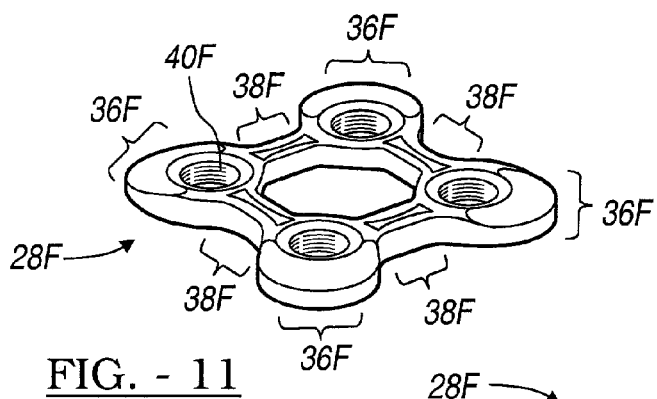
FIG. 11 is a perspective view of an elongated plate according to a further embodiment of the present invention, the elongated plate having four bridge regions with each bridge region coupled to two or more bone fixation regions so as to produce an overall square configuration.
Figure 11A:
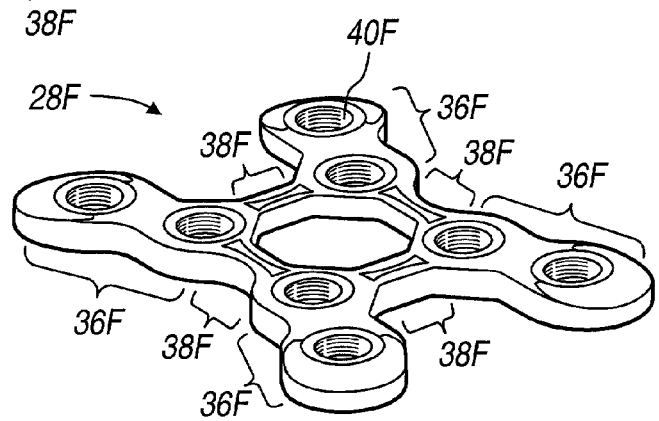
FIG. 11a is a perspective view of the elongated plate of FIG. 11 having multiple apertures extending at an angle from the bridge region.
Figure 11B:
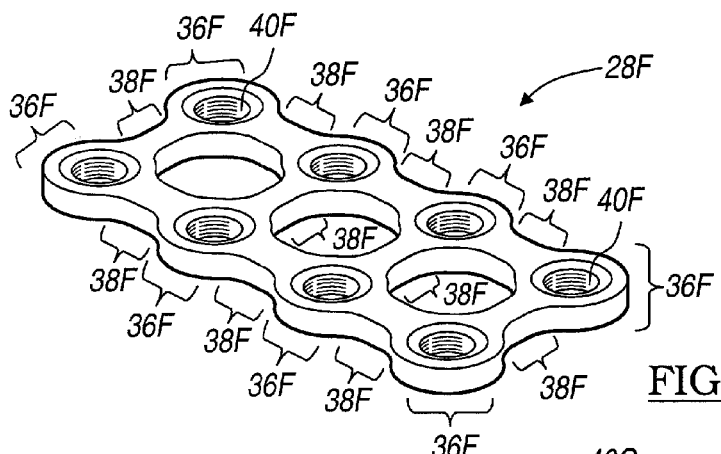
FIG. 11b is a perspective view of the elongated plate of FIG. 11 having additional bridge regions terminating in bone fixation regions, the additional bridge regions terminating in bone fixation regions are configured so as to produce an overall configuration having the shape of a rectangle.

Referring to FIG. 11, an elongated plate 28F according to the teachings of still a further embodiment of the present invention is shown. Elongated plate 28F is generally similar to elongated plate 28 and thus a detailed description of plate 28F is not necessary. However, unlike elongated plate 28, elongated plate 28F includes multiple bridge regions 38F. Specifically, FIG. 11 illustrates four bridge regions 38F each terminating in a pair of bone fixation regions 36F, the bridge regions 38F arranged at right angles to each other so that the elongated plate 28F has the overall shape of a square. As seen in FIG. 11a, each bone fixation region 36F may include one or more apertures 40F, with the second and subsequent apertures 40F extending at a zero to ninety degree angle and may extend at about a ten or eighty degree angle from each bridge region 38F. Further, as seen in FIG. 11b, elongated plate 28F may contain additional apertures 40F and bridge regions 38F extending from the configuration illustrated in FIG. 11 so as to produce an elongated plate 28F having additional affixation points for a fastener, such as fastener 44, to engage separated portions A and B of the sternum 16. The features of elongated plate 28F may be incorporated into any of the other embodiments of the present invention.

Figure 12:
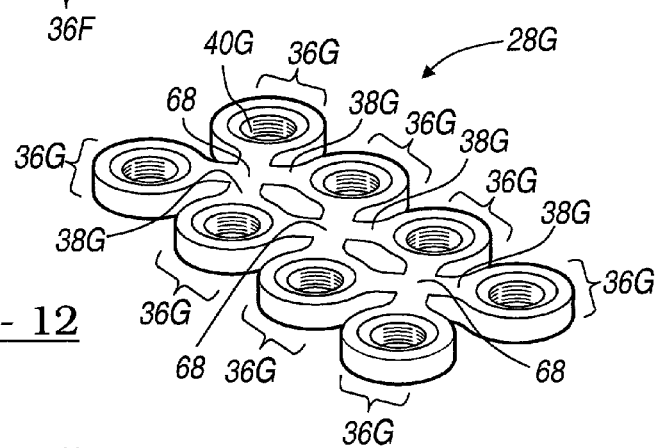
FIG. 12 is a perspective view of an elongated plate according to an additional embodiment of the present invention, the bone fixation regions coupled on one or more ends to one or more bridge regions with multiple bridge regions intersecting at a bridge region mid-point.

An additional embodiment of the present invention is illustrated in FIG. 12 in the form of elongated plate 28G. Elongated plate 28G is generally similar to elongated plate 28 and thus a detailed description is not necessary. Elongated plate 28G is also similar to plate 28F, as illustrated in FIG. 11b, in that plate 28G contains multiple bridge regions 38G connecting a plurality of bone fixation regions 36G. However, plate 28G is different from 28F as illustrated in FIG. 11b in that the bridge regions 38G intersect at an approximately ninety degree angle at a mid-point 68 as illustrated in FIG. 12. It must be noted that this embodiment may incorporate any of the other described embodiments of the current invention.

Figure 13:
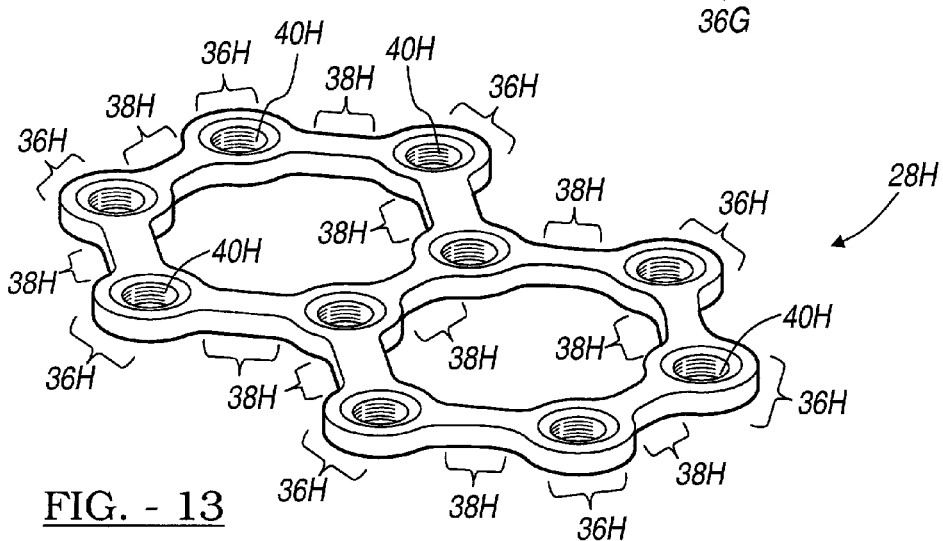
FIG. 13 is a perspective view of an elongated plate according to yet another embodiment of the present invention, the bone fixation regions are coupled on one or more ends to one or more bridge regions, the bridge regions arranged in the shape of two hexagons, the two hexagons sharing a common bridge region and two common apertures.
Figure 17:
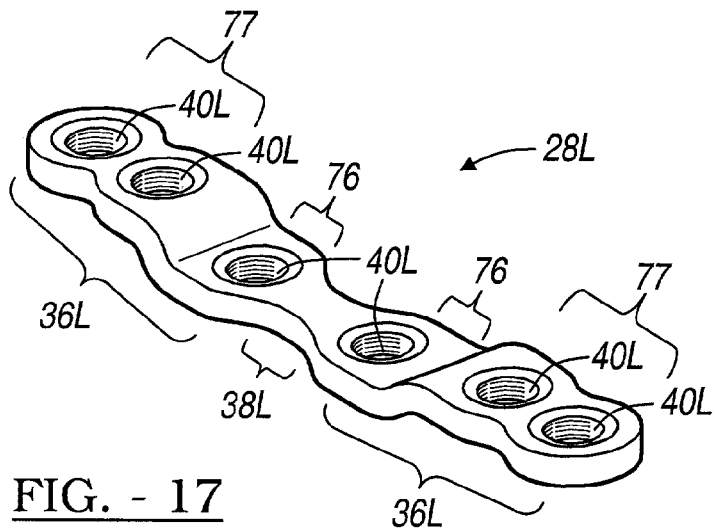
FIG. 17 is a perspective view of an elongated plate according to an additional embodiment of the present invention, the elongated plate having a bridge region and a portion of the bone fixation region located in a plane above or below the bone fixation region.

Yet an additional embodiment of the present invention is illustrated in FIG. 13 in the form of elongated plate 28H. Elongated plate 28H is generally similar to elongated plate 28 and thus a detailed description is not required. Elongated plate 28H is different from plate 28 in that the bridge regions 38H each terminating in bone fixation regions 36H are arranged in two hexagon configurations, with each hexagon sharing one common bridge region 38H as seen in FIG. 17. It must be noted that this embodiment may incorporate any of the other described embodiments of the current invention.

Figure 14:
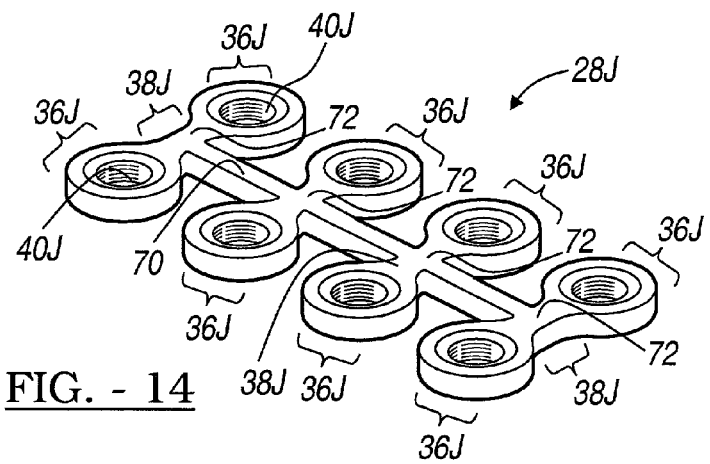
FIG. 14 is a perspective view of an elongated plate according to another embodiment of the present invention, the elongated plate having multiple bridge regions terminating in bone fixation regions arranged in a parallel relationship to each other and interconnected by a backbone at a mid-point of each bridge region.

A further embodiment of the present invention is illustrated in FIG. 14 in the form of elongated plate 28J. Elongated plate 28J is generally similar to elongated plate 28 and thus a detailed description of elongated plate 28J is not necessary. However, unlike elongated plate 28, elongated plate 28J includes of a plurality of bridge regions 38J each terminating in a bone fixation region 36J having at least one aperture 40J, and the bone fixation regions 36J interconnected by a backbone portion 70. The backbone portion 70 intersects each bone fixation region 36J at a mid-point 72 at a ninety degree angle. Elongated plate 28J may incorporate any of the other embodiments described in this invention.

Figure 15:
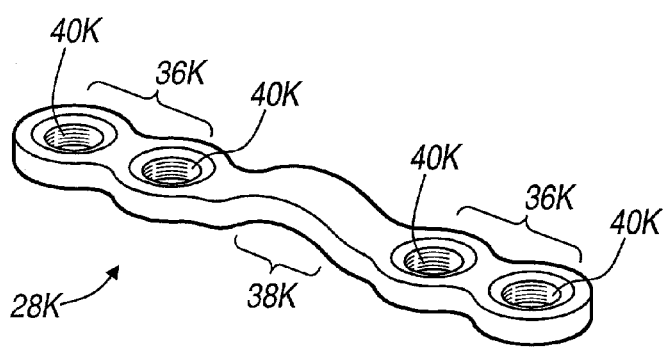
FIG. 15 is a perspective view of an elongated plate according to a further embodiment of the present invention, the elongated plate having an arched bridge portion.
Figure 16:
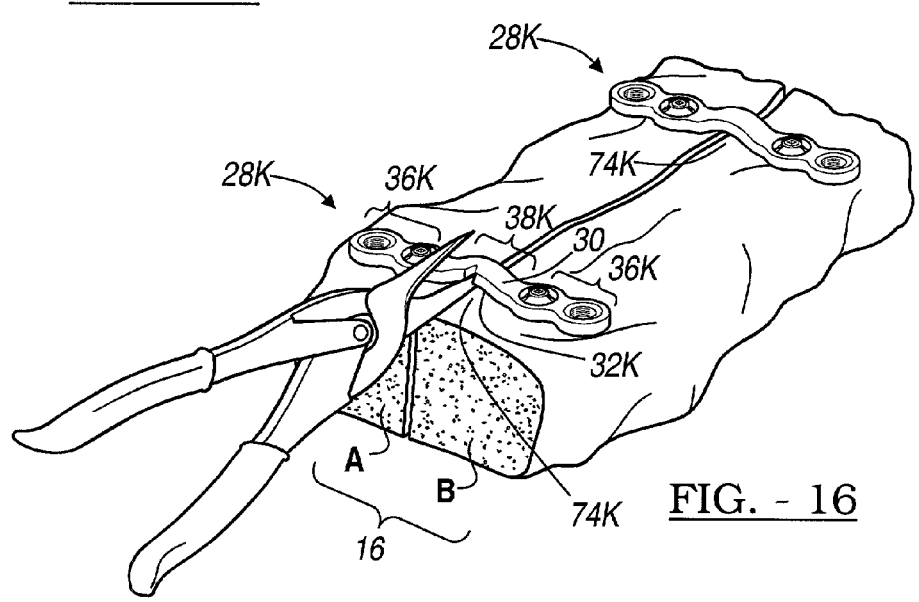
FIG. 16 is a perspective view of the elongated plate of FIG. 15, the elongated plate coupled to a sternum with the bridge portion of the elongated plate engaged by surgical scissors.

Referring to FIG. 15, an elongated plate 28K according to the teachings of an additional preferred embodiment of the present invention is shown. Elongated plate 28K is generally similar to elongated plate 28 and thus a detailed description of elongated plate 28K is not necessary. However, unlike elongated plate 28, elongated plate 28K has an arched bridge region 38K. As seen in FIG. 16, the presence of arched bridge region 38K forms a gap 74K between the elongated plate 28K and the sternum 16. The gap 74K allows both the upper surface 30K and the lower surface 32K of the arched bridge region 38K to be easily engaged by a cutting device such as surgical scissors 75 or wire cutters (not shown) so as to permit the scissors 75 or wire cutters to sever the elongated plate 28K by cutting arched bridge 38K. Consequently, elongated plate 28K permits physician access to the thoracic cavity 26 by either removing the head member 48 of fastener 44 or by severing the bridge region 38K. It must be noted that the arched bridge region 38K may be incorporated into any of the other described embodiments of the present invention.

FIG. 17 illustrates elongated plate 28L according to an embodiment of the present invention. The plate 28L is generally similar to plate 28 and thus a detailed description is not necessary. However, elongated plate 28L is different from plate 28 in that the bone fixation region 36L of elongated plate 28L includes a portion 76 disposed generally linearly with the bridge portion and a stepped portion 77 offset there from. Consequently, elongated plate 28L is able to couple severed bone regions A and B of sternum 16 that are not in the same plane or do not have a flat surface. Such a configuration may be incorporated into any of the other embodiments of the present invention.

Figure 18:
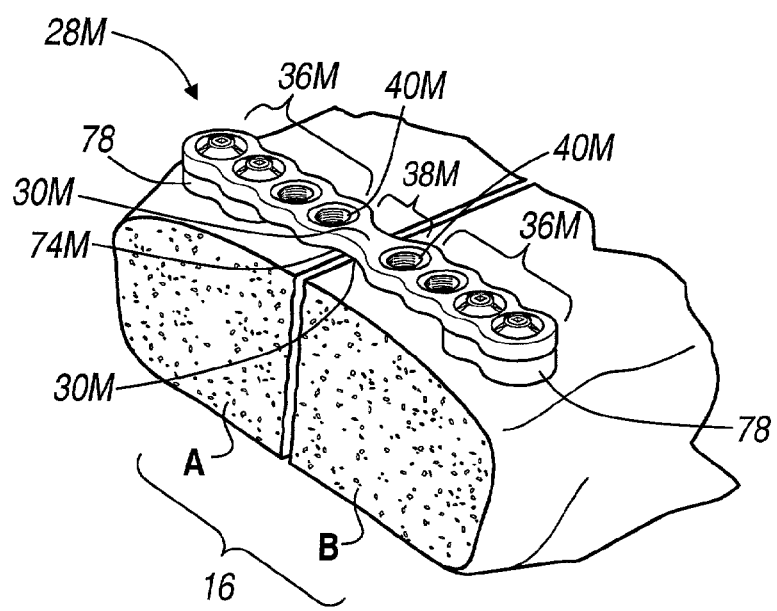
FIG. 18 is a perspective view of an elongated plate according to an additional embodiment of the present invention, the bone fixation regions of the elongated plate seated atop two feet.

FIG. 18 illustrates elongated plate 28M in accordance with an additional embodiment of the present invention. Elongated plate 28M is generally similar to elongated plate 28 and thus a detailed description of plate 28M is not necessary. However, elongated plate 28M is different from plate 28 in that elongated plate 28M is elevated above the sternum 16 so as to create a gap 74M similar to gap 74K. The gap 74M is due to the bone fixation regions being seated atop two feet 78. The two feet 78 contain a plurality of apertures 40M that are able to receive the fasteners 44 used to secure the elongated plate 28M to sternum 16. Like gap 74K, gap 74M allows the upper surface 30M, the lower surface 32M, and perimeter surface 34M of the arched bridge region 38M to be easily engaged by a cutting device such as surgical scissors 75, wire cutters or a cautery so as to permit the scissors 75, wire cutters or cautery to sever the bridge 38M. Consequently, elongated plate 28M permits physician access to the thoracic cavity 26 by removing either the head member of fastener 44 or by severing the bridge region 38M. It must be noted that the feet 78 of plate 28M may be used in conjunction with any of the other embodiments of the present invention so as to create a gap 74 between the elongated plate 28 and the sternum 16.

Figure 19:
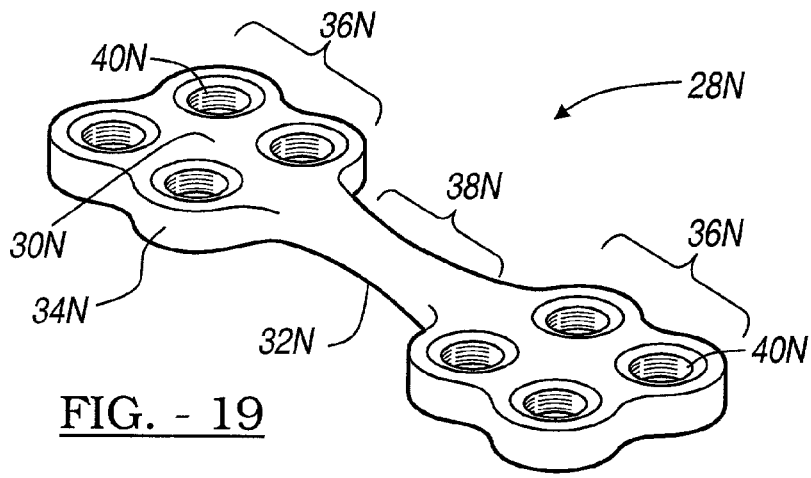
FIG. 19 is a perspective view of an elongated plate according to an additional embodiment of the present invention, the elongated plate having a tapered bridge region.
Figure 19A:
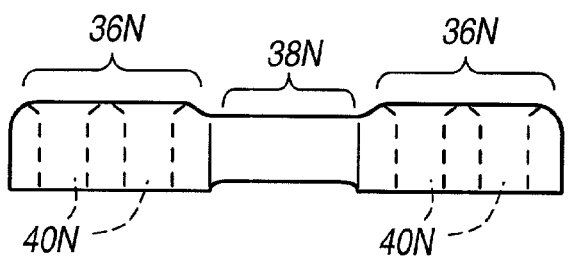
FIG. 19a is a side view of the elongated plate of FIG. 19.
Figure 19B:
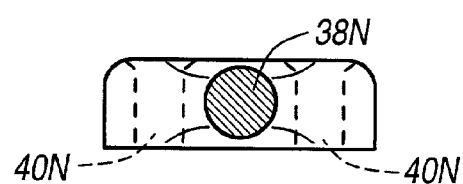
FIG. 19b is an end view of the elongated plate of FIG. 19.

FIG. 19 illustrates an elongated plate 28N in accordance with yet another embodiment of the present invention. Elongated plate 28N is generally similar to elongated plate 28 and thus a detailed description of elongated plate 28N is not necessary. However, unlike elongated plate 28, elongated plate 28N has a tapered bridge region 38N. The tapered bridge 38N is tapered such that the most narrow portion of the bridge 38N is preferably at a point halfway between the two bone fixation regions 36N. However, the most narrow portion of the bridge 38N may be at any point between the two bone fixation regions 36N.

Figure 19C:
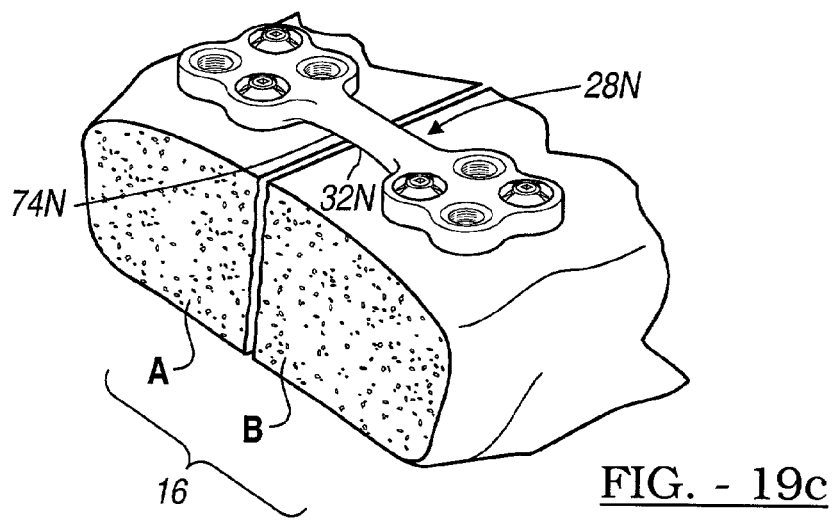
FIG. 19c is a perspective view of the elongated plate of FIG. 19, the elongated plate secured to reapproximated sternum halves A and B.

The bridge 38N may be tapered at its perimeter surface 34N, its upper surface 30N, or its lower surface 32N. Tapering of the upper surface 30N and the perimeter surface 34N weakens the bridge 38N allowing the bridge 38N to be severed more easily. Tapering of the lower surface 32N results in the formation of a gap 74N between the plate 28N and the sternum 16 as seen in FIG. 19c. The gap 74N advantageously permits the surgical scissors 75 or wire cutters to engage and sever the bridge 38N and the elongated plate 28N. It must be noted that while FIG. 19 illustrates elongated plate 28N as having a cylindrical bridge 38N, alternate embodiments may contain a bridge that is elliptical, oval, or of another cross-section shape that will facilitate engagement of the bridge by a suitable cutting device such as surgical scissors 75 or wire cutters. Further, it is envisioned that any of the other embodiments of the present invention may include a bridge region 38N that is cylindrical, elliptical, oval, square, or of another cross-section shape so as to facilitate engagement of the bridge by a suitable cutting device.

Figure 20:
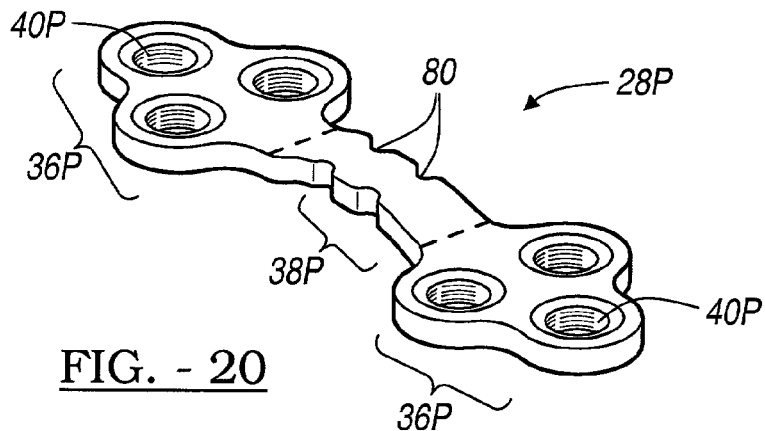
FIG. 20 is a perspective view of an elongated plate according to an additional embodiment of the present invention, the bridge region of the elongated plate having a notch.

FIG. 20 illustrates a elongated plate 28P according to the teachings of an additional embodiment of the present invention. Elongated plate 28P is generally similar to elongated plate 28 and thus a detailed description of elongated plate 28P is not necessary. However, unlike elongated plate 28, the bridge region 38P of elongated plate 28P has at least one notch 80. The notch 80 allows for a severing device, such as surgical scissors 75 or wire cutters, to more readily engage the bridge region 38P. Further, the notch 80 causes bridge region 38P to be weakened such that it can be severed using an amount of force less than that required to sever a bridge region 38 without notch 80. It must be noted that the notch 80 may be present in any of the other described embodiments of this invention.

Yet an additional embodiment of the present invention includes an elongated plate (not shown) having a pre-stressed or deformed bridge region formed by material treatment, selection, or geometry. The elongated plate of this embodiment is generally similar to elongated plate 28 and thus a detailed description of the elongated plate with the pre-stressed or deformed bridge region is not necessary. Material selection, such as resorbable material, for the bridge region can improve access to the gap and eases severing of the bridge region. Such a pre-stressed or deformed bridge region allows the device to be easily severed when subject to force produced by a suitable severing device such as surgical scissors 75 or wire cutters. Consequently, a physician is able to easily gain reentry to a patient's thoracic cavity to perform further surgery by applying minimal force and without removing the head member 48 of fastener 44. Such a pre-stressed or deformed bridge region may also be incorporated into any of the other embodiments of the present invention.

Figure 21:
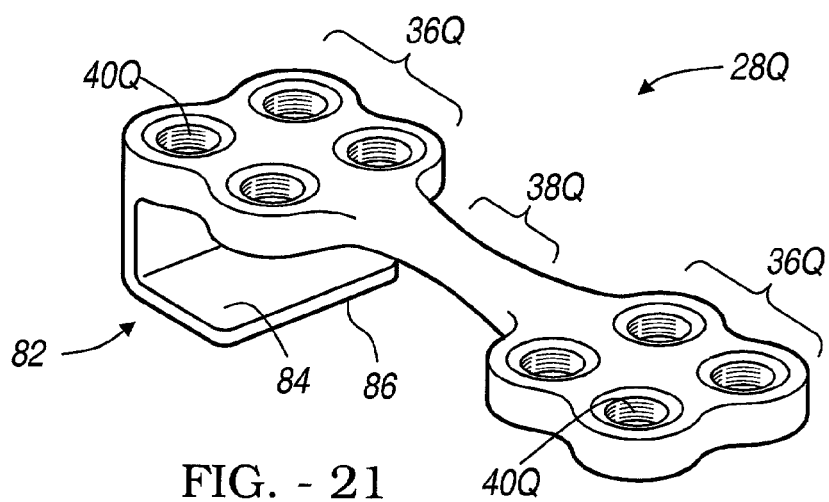
FIG. 21 is a perspective view of an elongated plate according to another embodiment of the present invention, the elongated plate having a hook.

Referring to FIG. 21, an elongated plate 28Q according to the teachings of an additional preferred embodiment of the present invention is shown. Elongated plate 28Q is generally similar to elongated plate 28 and thus a detailed description of elongated plate 28 is not necessary. However, unlike elongated plate 28, elongated plate 28Q includes at least one hook 82. The hook 82 is an extension of the elongated plate 28Q and is located at the end of one or more of the bone fixation regions 36Q.

The hook 82 includes a bone contact surface 84 and an outer surface 86. The hook 82 first extends from the bone fixation region 36Q at a right angle to the elongated plate 28Q for a distance slightly greater than the width of the sternum 16. The hook 82 then extends toward the bridge region 38Q of the elongated plate 28Q in a direction parallel to the elongated plate 28Q so as to engage the bone laterally. As a result of this configuration, the hook 82 is able to encompass the external portion of severed portion A or B of sternum 16. Consequently, elongated plate 28Q is better able to grip the reapproximated halves A or B of sternum 16 and is consequently better able to secure the halves A and B together to prevent movement of the halves A and B. It must be noted that any of the bone fixation regions 36 of any of the other embodiments of the current invention may be adapted to include hook 82.

Figure 22:
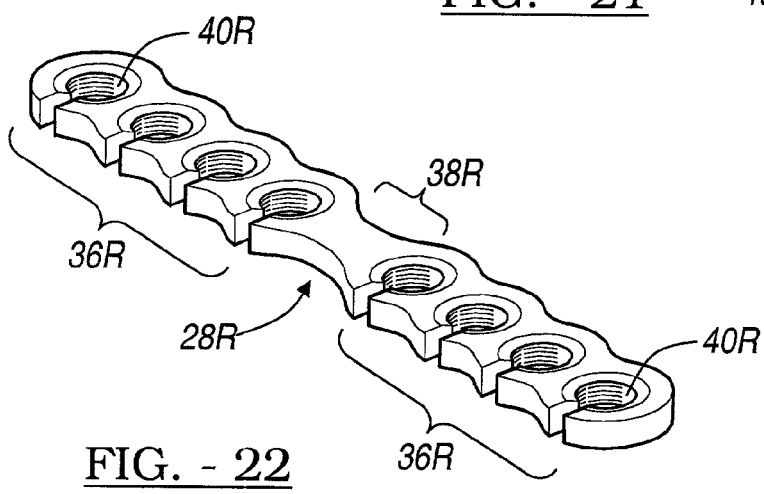
FIG. 22 is a perspective view of an elongated plate according to an additional embodiment of the present invention, the apertures of the elongated plate being open-ended.

FIG. 22 illustrates an elongated plate 28R representative of yet another embodiment of the present invention. Elongated plate 28R is generally similar to elongated plate 28 and thus a detailed description of elongated plate 28R is not necessary. However, unlike elongated plate 28, the apertures 40R of elongated plate 28R are open ended so as to include a slot 88 disposed between at least one of the apertures 40R and a perimeter surface of the plate 28R. The open apertures 40R act in the same manner as the apertures 40 of the other embodiments of this invention except that open apertures 40R allow for elongated plate 28R to be easily removed from engagement with the upper shaft portion 50 of fastener 44 once head member 48 has been removed. The open apertures 40P allow plate 28R to be removed from engagement with the upper shaft portion 50 in a lateral direction as opposed to being horizontally raised from the upper shaft portion 50. It is envisioned that apertures 40 of elongated plate 28R may be incorporated into any of the described embodiments of the current invention.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A sternal closure for coupling bone across a fracture or osteotomy, comprising:
    a plate having a lower surface facing the bone, an upper surface opposite the lower surface, and a perimeter surface between the upper surface and the lower surface, the plate including at least two bone fixation regions and a bridge region disposed between the bone fixation regions, each bone fixation region having at least one aperture; and
    a fastening device adapted to be disposed through the apertures and engaging the plate to secure the plate to one or more portions of bone;
    wherein the apertures are internally threaded; and
    wherein the fastening device includes an externally threaded lower shaft portion for engaging the bone, an externally threaded upper shaft portion, and a head member that is internally threaded for engaging the upper shaft portion.

2. The device of claim 1, wherein the bridge region includes a narrowed portion along at least one of the upper surface, lower surface and perimeter surface.

3. The device of claim 2, wherein the narrowed portion includes a cross-section selected from a group comprising: cylindrical, elliptical, oval, square.

4. The device of claim 1, wherein the bridge region tapers between the at least two bone fixation regions.

5. The device of claim 1, wherein the head member is externally threaded for engaging one of the internally threaded apertures.

6. The device of claim 1, wherein the fastener includes a flange portion between the lower shaft portion and the upper shaft portion.

7. The device of claim 1, wherein the fastening device is made from a bio-resorbable material.

8. The device of claim 1, wherein the fastening device is made from a bio-compatible material.

9. The device of claim 1, wherein the fastening device includes a pointed end portion.

10. The device of claim 1, wherein the bridge region is aligned so as to span the fracture or osteotomy.

11. The device of claim 1, wherein the bridge region is aligned so as to span the bone.

12. The device of claim 1, wherein the bone fixation regions are coupled on one or more ends to one or more intersecting bridge regions.

13. The device of claim 1, wherein the bone fixation regions are coupled on one or more ends to one or more bridge regions, one of the one or more bridge regions defining a common bridge region.

14. The device of claim 1, wherein the plate includes bio-compatible material.

15. A device for coupling bone across a fracture or osteotomy, comprising:
    a first bone fixation region having a first surface and a second surface that is opposite the first surface;
    a second bone fixation region having a third surface and a fourth surface that is opposite the third surface;
    a bridge region extending between the first bone fixation region and the second bone fixation region, the bridge region includes a fifth surface and a sixth surface that is opposite the fifth surface;
    an upper plane extending from the first surface to the third surface;
    a lower plane extending from the second surface to the fourth surface, the lower plane is opposite the upper plane, the lower plane contacts the bone when the device is mounted to the bone;
    a first gap between the fifth surface and the upper plane, the fifth surface proximate to and offset from the upper plane;
    a second gap between the sixth surface and the lower plane, the sixth surface proximate to and offset from the lower plane;

a first threaded aperture extending through the first bone fixation region from the first surface to the second surface; and a second aperture extending through the second bone fixation region from the third surface to the fourth surface.

16. The device of claim 15, further comprising a fastening device adapted to be disposed through the first threaded aperture and the second aperture and engage the device to secure the first and second bone fixation regions to one or more portions of bone.

17. The device of claim 16, wherein the fastening device is comprised of an externally threaded lower shaft portion for engaging a bone, an externally threaded upper shaft portion, and a head member that is internally threaded for engaging the upper shaft portion.

18. The device of claim 17, wherein the head member is externally threaded for engaging said first threaded aperture.

19. The fastening device of claim 17, wherein the fastener includes a flange portion between the lower shaft portion and the upper shaft portion.

20. The device of claim 16, wherein the fastening device is made from a bio-resorbable material.

21. The device of claim 16, wherein the fastening device is made from a bio-compatible material.

22. The device of claim 16, wherein the fastening device includes a pointed end portion.

23. The device of claim 15, wherein said second aperture is threaded.

24. The device of claim 15, wherein the bridge region is aligned so as to span the fracture or osteotomy.

25. The device of claim 15, wherein the bridge region is aligned so as to span the bone.

26. The device of claim 15, wherein the bone fixation regions are coupled on one or more ends to one or more intersecting bridge regions.

27. The device of claim 15, wherein the bone fixation regions are coupled on one or more ends to one or more bridge regions, one of the one or more bridge regions defining a common bridge region.

28. The device of claim 15, wherein the device includes bio-compatible material.

29. The device of claim 15, wherein said bridge region further comprises a first perimeter surface and a second perimeter surface opposite the first perimeter surface, the first and second perimeter surfaces are between the fifth and sixth surfaces;

wherein the first bone fixation region further comprises a third perimeter surface and a fourth perimeter surface opposite the third perimeter surface, the third and fourth perimeter surfaces are between the first and second surfaces;

wherein the second bone fixation region further comprises a fifth perimeter surface and a sixth perimeter surface opposite the fifth perimeter surface, the fifth and sixth perimeter surfaces are between the third and fourth surfaces;

wherein the first perimeter surface is recessed within the third and fifth perimeter surfaces; and wherein the second perimeter surface is recessed within the fourth and sixth perimeter surfaces.

30. The device of claim 15, wherein said bridge region has a generally cylindrical cross-section.

31. A device for coupling bone across a fracture or osteotomy comprising:

a first bone fixation region having a first surface and a second surface that is opposite the first surface;

a second bone fixation region having a third surface and a fourth surface that is opposite the third surface;

a bridge region extending between the first bone fixation region and the second bone fixation region, the bridge region includes a fifth surface and a sixth surface that is opposite the fifth surface, the fifth surface is recessed relative the first and third surfaces to form a first gap, the sixth surface is recessed relative the second and fourth surfaces to form a second gap;

a first threaded aperture extending through the first bone fixation region from the first surface to the second surface; and a second aperture extending through the second bone fixation region from the third surface to the fourth surface.

32. The device of claim 31, wherein the fifth surface is proximate to the second and fourth surfaces and distal to the first and third surfaces.

33. The device of claim 31, wherein the sixth surface is proximate to the first and third surfaces and distal to the second and fourth surfaces.

34. The device of claim 31, further comprising a fastening device operable to cooperate with each of the first and second apertures and engage the bone.

35. The device of claim 34, wherein the fastening device is comprised of an externally threaded lower shaft portion for engaging a bone, an externally threaded upper shaft portion, and a head member that is internally threaded for engaging the upper shaft portion.

36. The device of claim 35, wherein the head member is externally threaded for engaging said first threaded aperture.

37. The device of claim 35, wherein the fastener includes a flange portion between the lower shaft portion and the upper shaft portion.

38. The device of claim 34, wherein the fastening device is made from a bio-resorbable material.

39. The device of claim 34, wherein the fastening device is made from a bio-compatible material.

40. The device of claim 34, wherein the fastening device includes a pointed end portion.

41. The device of claim 31, wherein said second aperture is threaded.

42. The device of claim 31, wherein the bridge region is aligned so as to span the fracture or osteotomy.

43. The device of claim 31, wherein the bridge region is aligned so as to span the bone.

44. The device of claim 31, wherein the bone fixation regions are coupled on one or more ends to one or more intersecting bridge regions.

45. The device of claim 31, wherein the bone fixation regions are coupled on one or more ends to one or more bridge regions, one of the one or more bridge regions defining a common bridge region.

46. The device of claim 31, wherein the plate includes bio-compatible material.

47. The device of claim 31, further comprising a longitudinal axis extending through a center of the bridge region from the first bone fixation region to the second bone fixation region;

wherein the bridge region further comprises a first perimeter surface and a second perimeter surface opposite the first perimeter surface;

wherein the first bone fixation region further comprises a third perimeter surface and a fourth perimeter surface opposite the third perimeter surface;

wherein the second bone fixation region further comprises a fifth permeter surface and a sixth perimeter surface opposite the fifth perimeter surface; and wherein the first and second perimeter surfaces are closer to the longitudinal axis than each of the third, fourth, fifth, and sixth perimeter surfaces.

48. The device of claim 47, wherein the bridge region has a generally cylindrical cross-section.

* * * * *